United States Patent

Schnaibel et al.

Patent Number: 5,291,417
Date of Patent: Mar. 1, 1994

[54] METHOD AND ARRANGEMENT FOR DETERMINING THE INTERNAL RESISTANCE OF A LAMBDA PROBE AND FOR THE CLOSED-LOOP HEATING CONTROL WITH THE AID OF THE INTERNAL RESISTANCE

[75] Inventors: Eberhard Schnaibel, Hemmingen; Lothar Raff, Hochberg; Michael Westerdorf, Möglingen; Manfred Homeyer, Markgröningen, all of Fed. Rep. of Germany

[73] Assignee: Robert Bosch GmbH, Stuttgart, Fed. Rep. of Germany

[21] Appl. No.: 684,896
[22] PCT Filed: Oct. 6, 1989
[86] PCT No.: PCT/DE89/00638
§ 371 Date: Apr. 22, 1991
§ 102(e) Date: Apr. 22, 1991
[87] PCT Pub. No.: WO90/04778
PCT Pub. Date: May 3, 1990

[30] Foreign Application Priority Data
Oct. 22, 1988 [DE] Fed. Rep. of Germany ....... 3836045

[51] Int. Cl.$^5$ .................. G06F 15/20; G01R 27/00
[52] U.S. Cl. ................. 364/482; 364/571.01; 364/571.05; 324/600
[58] Field of Search ........ 364/571.01, 571.07, 364/431.06, 482, 557, 571.05; 123/688, 689; 73/116; 324/600, 691

[56] References Cited

U.S. PATENT DOCUMENTS

| | | |
|---|---|---|
| 4,419,190 | 12/1983 | Dietz et al. |
| 4,471,448 | 9/1984 | Williams ................. 364/151 X |
| 4,523,084 | 6/1985 | Tamura et al. ............ 364/482 X |
| 4,742,808 | 5/1988 | Blümel et al. .................. 123/489 |
| 4,930,095 | 5/1990 | Yuchi et al. ............... 364/571.01 |
| 5,095,453 | 3/1992 | Pierson et al. ............ 364/571.01 |
| 5,140,535 | 8/1992 | Raff et al. ................ 364/571.07 |

Primary Examiner—Kevin J. Teska
Attorney, Agent, or Firm—Walter Ottesen

[57] ABSTRACT

The internal resistance of a lambda probe is determined by: the application of a clocked direct-current counter voltage to the probe via a series resistor; the measurement of the output voltages with the counter voltage connected and disconnected; and, the calculation of the internal resistance from the measured values and known resistance values.

Apart from the components of a conventional arrangement, this method requires only a series resistor and a switch for implementation. Measurement can be carried out at short time intervals without excessively high direct-current voltage loading which affects the service life.

The internal resistance measured is compared with a desired resistance and the control deviation determined in this way is used to determine the duty factor for probe heating clocked with fixed frequency.

6 Claims, 1 Drawing Sheet

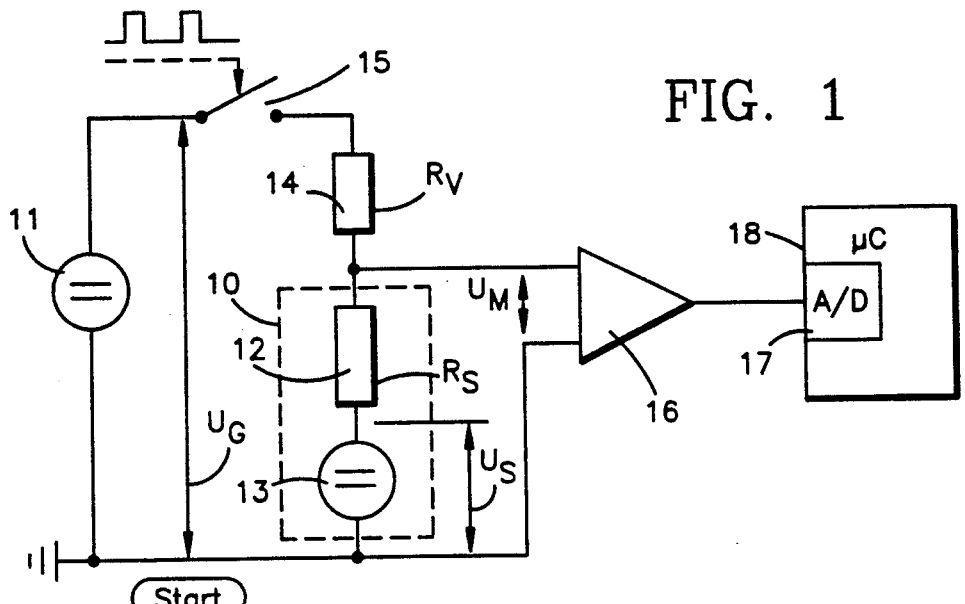
FIG. 1
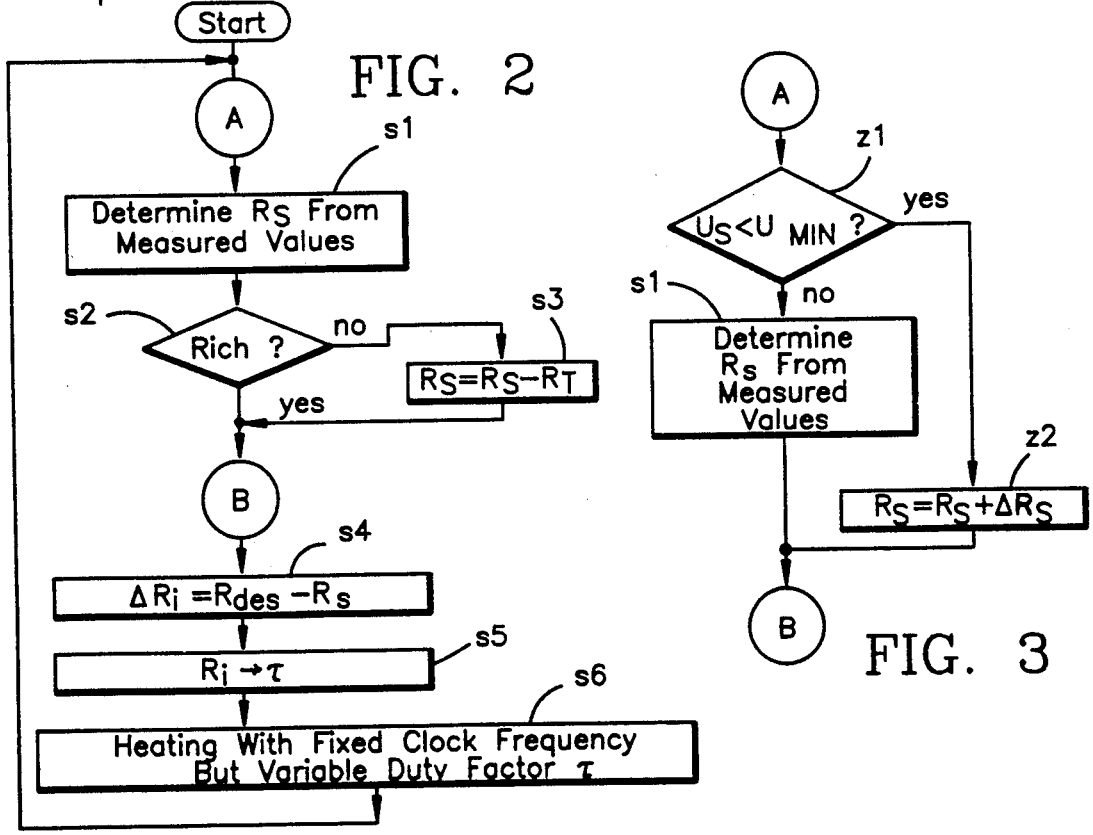
FIG. 2
FIG. 3

METHOD AND ARRANGEMENT FOR DETERMINING THE INTERNAL RESISTANCE OF A LAMBDA PROBE AND FOR THE CLOSED-LOOP HEATING CONTROL WITH THE AID OF THE INTERNAL RESISTANCE

FIELD OF THE INVENTION

The invention relates to a method and an arrangement for determining the internal resistance of a lambda probe with the aid of the output voltage values supplied by a lambda probe circuit. The invention furthermore relates to a method for the closed-loop heating control with the aid of the internal resistance determined.

BACKGROUND OF THE INVENTION

U.S. Pat. No. 4,419,190 discloses a method according to which the internal resistance is measured with the aid of an alternating current passed through the probe. The alternating voltage component is separated from the direct voltage component of the probe and the internal resistance is determined from alternating current and alternating voltage. The frequency used is preferably about 5,000 Hz. From the difference between the measured internal resistance and a desired value of the internal resistance, a control deviation is formed with the aid of which heating of the probe is controlled. The disadvantage of this method for measuring the internal resistance is that a separate alternating current source and a separate alternating voltage evaluating circuit are required. An advantage is that no burden is placed on the probe voltage by the determination of the internal resistance, with the result that the internal resistance can be determined at very short time intervals.

U.S. Pat. No. 4,742,808 discloses a method for determining the internal resistance of a lambda probe, according to which the probe is periodically loaded by electrically connecting a load resistor. The internal resistance is calculated with the aid of the load resistor from the voltages measured in the loaded condition and in the unloaded condition. The value of the load resistor is compared to a threshold value to determine whether the probe is ready for operation. This method requires minimal circuit complexity since only the load resistor and a switch are required. A disadvantage is that the probe voltage recovers only relatively slowly after loading, with the result that the internal resistance cannot be measured by this method when the lambda probe is involved in control operations. In that case, the probe voltage must be measured approximately every 10 to 15 ms. However, after loading, the probe voltage only recovers in a time span of about 100 ms.

SUMMARY OF THE INVENTION

The invention has the object of providing a method for determining the internal resistance of a lambda probe which can be implemented with little circuit complexity and does not impair the normal measurement of the probe voltage. It is the further object of the invention to provide an arrangement for carrying out such a method. A further object is to indicate a method of using the determined internal resistance for the purpose of closed-loop heating control. The determined internal resistance is corrected taking into account a predetermined relationship with lean and rich lambda values. This teaching is based on the realization that, when the lambda values jump from rich to lean and vice versa, the internal resistance likewise changes abruptly even though the temperature of the probe does not change. The teaching can be used, inter alia, to ensure that the probe heating power is not altered abruptly when the internal resistance changes due to a jump in the lambda value instead of a change in temperature.

The method according to the invention for determining internal resistance is characterized in that a clocked direct-current counter voltage is applied to the lambda probe via a series resistor. The output voltage of the lambda probe circuit is measured with the counter voltage connected and disconnected and, taking into account known resistance values of the circuit, the internal resistance is calculated from the two voltage values measured. Compared to a conventional device, the only additional components required for this purpose by the arrangement according to the invention are a direct-current voltage source with a series resistor and a switch.

With the aid of the internal resistance measured, a control deviation value for the internal resistance is determined in a known manner. This value is used in accordance with the method according to the invention for the closed-loop heating control to alter the duty factor of a clocked heating voltage supply. If the internal resistance is determined with the aid of a method which cannot be used at very lean lambda values, that is in particular during overrun operation, the actual value of the internal resistance is, in accordance with an advantageous further development, automatically increased in steps. This ensures that when the probe is in danger of cooling during overrun operation, the mean heating power is increased even though the internal resistance cannot be determined at that precise moment.

BRIEF DESCRIPTION OF THE DRAWINGS

The invention is explained in greater detail below with reference to embodiments illustrated by figures, of which:

FIG. 1 shows a circuit diagram of an arrangement for determining the internal resistance of a lambda probe;

FIG. 2 shows a flow diagram of a method for the closed-loop control of heating; and, FIG. 3 shows a component flow diagram for explaining a part-method according to which the actual value of the internal resistance of the probe is automatically increased during overrun operation.

DESCRIPTION OF THE PREFERRED EMBODIMENTS OF THE INVENTION

The circuit diagram according to FIG. 1 contains the equivalent circuit diagram of a probe 10. The equivalent circuit diagram includes a probe direct-current voltage source 13, which supplies the probe voltage $U_S$, and the probe internal resistance 12 having the resistance value $R_S$. A counter voltage of the value $U_G$ can be applied to the probe 10 via a switch 15 by a direct-current counter voltage source 11 with a series resistor 14 having the value $R_V$. The switch is preferably realized by a semiconductor component, in particular a transistor. The switch is opened and closed in a clocked manner, this being indicated by a pulse train. Preferably, the switch is closed every 10 ms for 300 $\mu$s.

The voltage, which falls between the connections of the probe, is supplied to a differential amplifier 16 which supplies its output voltage to an A/D converter 17, which is part of a microcomputer 18.

As long as the switch 15 is closed, the current I flows in the circuit containing the mentioned resistors and voltage sources. The following measurement voltage $U_M$ then drops off between the connections of the probe:

$$U_M = IR_S + U_S \qquad (1)$$

The following relationship also applies:

$$U_G = IR_V + IR_S + U_S \qquad (2)$$

If equation (1) is solved for the current I and this value is substituted in equation (2), the following is obtained for the internal resistance $R_S$ of the probe:

$$R_S = R_V(U_M - U_S)/(U_G - U_M) \qquad (3)$$

The voltage $U_M$ is the voltage measured with the switch closed, while the voltage $U_S$ is the voltage with the switch open, that is with the probe de-energized. The value of the counter voltage, preferably +5V, and the value $R_V$ of the series resistance are known. The value $R_S$ of the internal resistance can thus be calculated from equation (3).

Because of the ambient conditions around the lambda probe, it is undesirable to measure resistance values greater than 1 Mohm since, for example, air moisture and dirt would too greatly falsify the measurement result. In the case of resistances <10 ohm, the current becomes so great that self-heating cannot be ignored. Since the series resistor and the internal resistance of the probe are connected in series and can be regarded and measured as voltage dividers, the two values must not differ too much from one another. It has proven advantageous if the internal resistance of the probe differs by no more than a factor or quotient of 10 from the series resistance. Using a series resistor, a range of two powers of ten of the internal resistance of the probe is thus covered. The range of resistance discussed, from 10 ohms (probe temperature about 900° C.) to 1 Mohm (probe temperature about 250° C.) covers five powers of ten, for which reason three different series resistors are required, that is 68 ohms, 3.3 kohms and 150 kohms. If a measurement is to be carried out only in the usual range of operating temperatures from about 650° to 900° C., it is sufficient to use the series resistor with the smallest value.

The clocked application of the direct-current counter voltage constitutes a direct-current loading of the lambda probe 10. At the voltage resistance and duty factor values given, however, the loading is so small that the life of the probe is unaffected thereby. A further side effect of the loading with direct current to be noted is that the probe voltage $U_S$ increases by about 50 to 100 mV compared to the unloaded condition. The additional voltage builds up in about 10 seconds after the connection of the clocked direct-current voltage and decays in a similar time when it is disconnected. Since this shift is fixed, it can be taken into account in the evaluation of the probe signal.

Under certain circumstances, the voltage increase just described stems from a polarization effect. This voltage shift should be distinguished from that which occurs in the circuit explained at the beginning for determining internal resistance, in which the probe is loaded with a load resistor. There the probe voltage falls markedly with each loading and recovers in a time span of about 100 ms. This latter time response, which prevents measurements following in rapid succession, is absent in the case of the method described with reference to FIG. 1.

With the aid of the method described, the determination was made that the internal resistance of the probe not only depends on the temperature of the probe but also on whether the lambda value is lean or rich. It is of little importance how rich or how lean the lambda value is. The jump from lean to rich and vice versa, even if this jump is relatively small, is associated with the occurrence of a jump in the value of the internal resistance. The differential value is as large as that which also occurs in the case of a temperature jump of about 5° to 10° C. Since, in most applications, the internal resistance is only measured to determine with its aid the value of a temperature-dependent variable, it is advantageous to correct the internal resistance determined, taking into account the lambda value. In the embodiment according to FIG. 2, this is accomplished after a step s1, in which the value $R_S$ of the internal resistance has been determined, by a check in a step s2 to establish whether the lambda value is rich. If this is the case, the particular value of the internal resistance is used further without being altered. If, on the other hand, the lambda value is not rich, the value determined is increased in a step s3 by a predetermined difference $\Delta R_m$. It is only the increased value which is used for further measures. This sequence ensures that the resistance value subsequently used can be indicated to be constant despite the lambda jump so that, triggered by the lambda jump and thus the actual jump in the resistance value, the illusion of a temperature jump is not given.

The temperature dependence of the internal resistance is, for example, used for closed-loop heating control as described in U.S. Pat. No. 4,419,190 mentioned in the beginning, for determining the point in time at which the probe is ready, as described in U.S. Pat. No. 4,742,808 mentioned in the beginning, or for the temperature-dependent correction of the lambda value, as indicated in U.S. Pat. No. 5,140,535 (not published previously). With reference to the already partially explained flow diagram of FIG. 2 it will now be explained how measured values of the internal resistance are used for the closed-loop control of heating.

The steps s2 or s3 already mentioned are followed by a step s4, in which a control deviation value $\Delta R_i$ is formed by subtracting the value $R_S$ of the determined internal resistance of the probe from a desired value $R_{des}$. In a step s5, the control deviation value is used to determine a duty factor $\tau$, specifically such that, the smaller the actual value of the internal resistance compared to the desired value, the smaller the duty factor becomes. This ensures in a step s6, that a heating voltage supply clocked at a constant frequency heats the probe less, the smaller is the internal resistance of the probe, that is, the higher the actual temperature lies above the desired temperature. Step s6 is once more followed by step s1, that is, a new determination of the current value of the internal resistance.

In FIG. 2, a mark A is drawn in ahead of step s1 and a mark B after step s1. A variant of the method sequence between the marks A and B is shown in FIG. 3. The reason for this variant is as follows.

If the method explained with reference to FIG. 1 or that in accordance with U.S. Pat. No. 4,419,190 is used for determining the internal resistance, reliable measurement values are obtained even in the case of overrun operation. In the case of the method according to U.S. Pat. Nos. 4,742,808 and 5,140,535, on the other hand, reliable determination is no longer possible when both the voltage of the unloaded and of the loaded probe each assumes a very low value of only a few mV, as is the case with operation in the very lean range, that is in particular during overrun operation. However, if no internal resistance can be measured, the desired-value/actual-value comparison according to step s4 is not possible. The variant according to FIG. 3 therefore makes provision for a check in a step z1 to determine whether the probe voltage $U_S$ has fallen below a minimum voltage $U_{MIN}$. If this is not the case, the step s1 already explained follows, whereupon the mark B is reached. On the other hand, if this is the case, the value $R_S$ of the internal resistance of the probe determined in the previous pass is increased by a predetermined differential value $\Delta R_S$ in a step z2. After this, the mark B is reached again. The measure according to step z2 guarantees that a higher and higher actual value of the internal resistance and thus a lower and lower probe temperature is indicated even though the actual value cannot be determined at all. It is thereby ensured that the probe heating power is increased in order to counteract the cooling caused by overrun operation.

Attention is drawn to the fact that the method explained above with reference to FIG. 1 can also be used when the probe circuit is not of such a simple design as in FIG. 1. FIG. 1 shows the simplest possible case, namely a voltage tap directly at the probe connections. In practice, however, it is customary to permanently counter-connect a reference voltage to the probe. Whenever the probe voltage crosses a voltage close to the reference voltage or coinciding with the latter, a change in the direction of control occurs. A clocked direct-current counter voltage can also be connected in addition to the probe via a series resistor in the case of such a lambda probe circuit. The evaluation equations are then somewhat more complicated than equations (1) to (3) given above since the value of the permanently applied reference voltage and of the load resistance enter into them as well.

The direct-current counter voltage source 13 is advantageously obtained by voltage division of a voltage such as that which is supplied by a voltage source present in any case. Preferably, the output voltage of a highly accurate reference voltage source is used, such as that which is present in closed-loop engine control devices in any case.

We claim:

1. A computer-implemented method for controlling heating of a lambda probe equipped with heater control and having a temperature dependent actual internal resistance $R_S$, said method including the steps of:

(a) comparing the probe voltage $U_S$ to a predetermined threshold $U_{min}$ below which the actual internal resistance value can no longer be reliably determined and determining said actual internal resistance value when said probe voltage $U_S$ is higher than said threshold $U_{min}$;

(b) forming a variable imaginary internal resistance value by incrementally increasing an initial internal resistance value in steps by a pregiven difference value $\Delta R_S$ while assuming that said initial resistance value matches said actual internal resistance value when said probe voltage $U_S$ falls below said threshold $U_{min}$;

(c) obtaining a control deviation value $\Delta R_i$ by forming the difference of said variable imaginary internal resistance value and a predetermined desired internal resistance value corresponding to a desired probe temperature when said probe voltage $U_S$ is less than said threshold $U_{min}$ or by forming the difference of the determined actual internal resistance value and said predetermined desired internal resistance value when said probe voltage $U_S$ is higher than said threshold $U_{min}$;

(d) forming an actuating variable from control deviation value $\Delta R_i$ for said heater control; and, (e) applying said actuating variable to the probe to control the heating.

2. The computer-implemented method of claim 1, wherein said lambda probe is cyclically heated at a frequency between 20 and 100 Hz.

3. The computer-implemented method of claim 1, wherein said lambda probe provides an instantaneous value of lambda, said method comprising the further step of correcting said actual internal resistance value in dependence upon the instantaneous value of lambda.

4. The computer-implemented method of claim 1, wherein said lambda probe is part of a lambda probe circuit and said actual internal resistance value of the lambda probe is determined with the aid of the output voltage value supplied by the lambda probe circuit by: applying a clocked direct-current counter voltage to said circuit via a series resistor, measuring the value of said output voltage when the counter voltage is switched so as to be applied to and removed from said circuit; and, computing said actual internal resistance value from the following: the measured values of the output voltage; and, the value of the series resistor and the value of the counter voltage.

5. The computer-implemented method of claim 4, wherein a low pulse duty factor is used while clocking the counter voltage in order to keep the direct-current voltage load on the probe as low as possible.

6. The computer-implemented method of claim 5, wherein a clock frequency of 100 Hz at a switch-on duration of 300 $\mu s$ is used.

* * * * *